United States Patent
Lorenzini et al.

(10) Patent No.: US 10,736,675 B2
(45) Date of Patent: Aug. 11, 2020

(54) ENDOSSEOUS SCREW ASSEMBLY AND INTERNAL FIXATION SYSTEM COMPRISING SAID ENDOSSEOUS SCREW ASSEMBLY

(71) Applicant: Orthofix S.R.L., Verona (IT)

(72) Inventors: Denis Lorenzini, Verona (IT); Federico Vicenzi, Trento (IT)

(73) Assignee: Orthofix S.R.L., Verona (IT)

( * ) Notice: Subject to any disclaimer, the term of this patent is extended or adjusted under 35 U.S.C. 154(b) by 94 days.

(21) Appl. No.: 15/764,866

(22) PCT Filed: Sep. 19, 2016

(86) PCT No.: PCT/EP2016/072100
§ 371 (c)(1),
(2) Date: Mar. 29, 2018

(87) PCT Pub. No.: WO2017/055117
PCT Pub. Date: Apr. 6, 2017

(65) Prior Publication Data
US 2019/0038325 A1 Feb. 7, 2019

(30) Foreign Application Priority Data

Sep. 29, 2015 (EP) ..................................... 15425073

(51) Int. Cl.
*A61B 17/72* (2006.01)
*A61B 17/86* (2006.01)
(Continued)

(52) U.S. Cl.
CPC .......... *A61B 17/725* (2013.01); *A61B 17/744* (2013.01); *A61B 17/8685* (2013.01);
(Continued)

(58) Field of Classification Search
CPC .................... A61B 17/62; A61B 17/72; A61B 17/7208–7241; A61B 17/725; A61B 17/8894
See application file for complete search history.

(56) References Cited

U.S. PATENT DOCUMENTS 6,443,945 B1 * 9/2002 Marchitto .............. A61B 5/411
128/897
2002/0143333 A1 * 10/2002 von Hoffmann ...... A61B 17/68
606/67
(Continued)

FOREIGN PATENT DOCUMENTS

JP 2002065687 A 3/2002
WO 2004110292 A2 12/2004

OTHER PUBLICATIONS

International Search Report and Written Opinion of the International Searching Authority dated Dec. 23, 2016 in connection with International Application No. PCT/EP2016/072100, 9 pages.

*Primary Examiner* — Tessa M Matthews
(74) *Attorney, Agent, or Firm* — Haynes and Boone, LLP

(57) ABSTRACT

An endosseous screw assembly for an internal fixation system, comprising: a stem extending longitudinally and having at least one threaded distal portion for allowing anchoring to a bone site of a patient; a connection sleeve suitable for introduction inside a connection hole of a fixation member; and a ring nut rotatably mounted on the connection sleeve. The ring nut may be threadably mounted on the connection sleeve and may comprise a rim with teeth designed to cooperate with a step formed on the fixation member, in the vicinity of the connection hole, so as to prevent rotation of the ring nut with respect to the fixation member when the connection sleeve is introduced into the connection hole of the fixation member. The ring nut may further comprise multiple deformable interference fit com- (Continued)

ponents which lie along a conical portion of the connection sleeve.

29 Claims, 6 Drawing Sheets

(51) Int. Cl.
*A61B 17/74* (2006.01)
*A61B 17/88* (2006.01)
*A61B 17/17* (2006.01)

(52) U.S. Cl.
CPC ...... *A61B 17/8875* (2013.01); *A61B 17/8894* (2013.01); *A61B 17/1721* (2013.01)

(56) References Cited

U.S. PATENT DOCUMENTS

| | | |
|---|---|---|
| 2006/0084999 A1 | 4/2006 | Aschmann |
| 2006/0089647 A1* | 4/2006 | Culbert ................. A61B 17/68 606/65 |
| 2008/0119856 A1* | 5/2008 | Gotfried ............ A61B 17/7225 606/67 |
| 2012/0191092 A1* | 7/2012 | Buettler ............. A61B 17/8891 606/64 |
| 2014/0214098 A1 | 7/2014 | Probe et al. |
| 2018/0250040 A1* | 9/2018 | Menci .................. A61B 17/725 |

\* cited by examiner

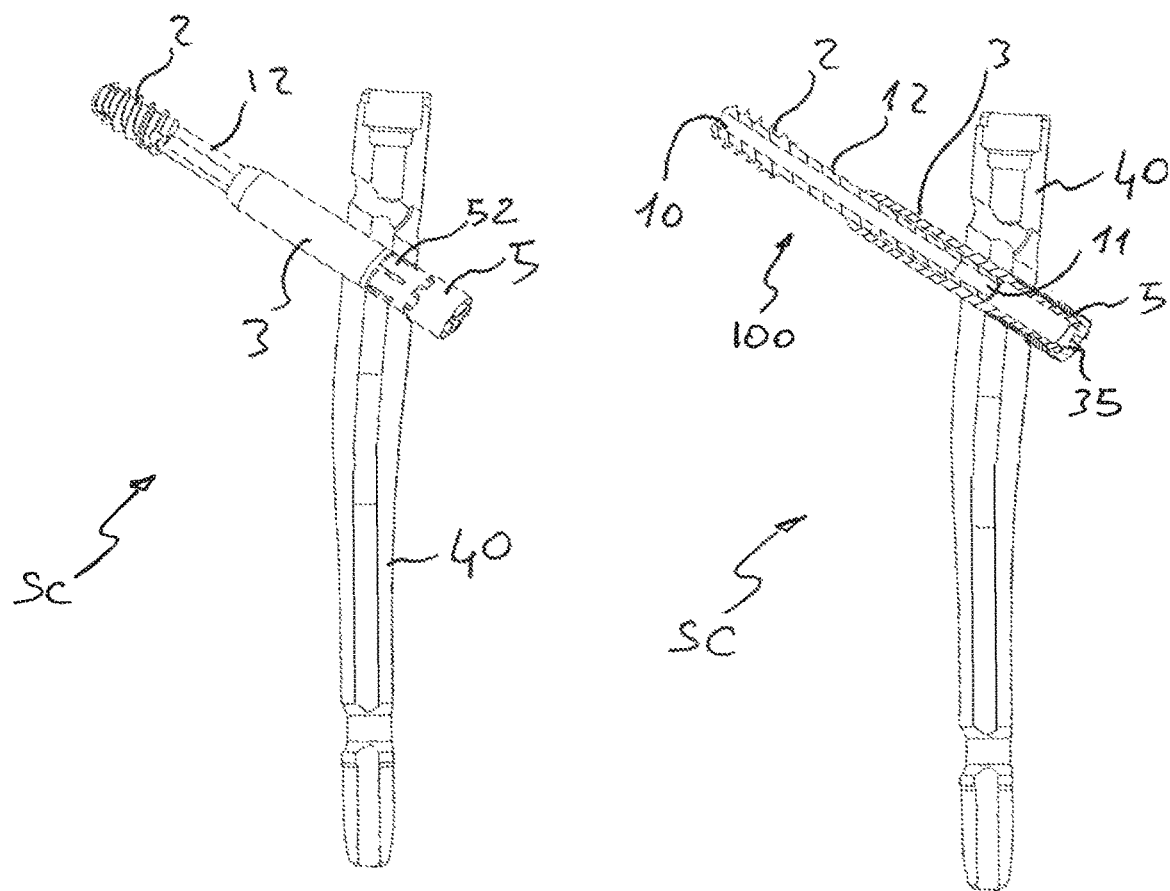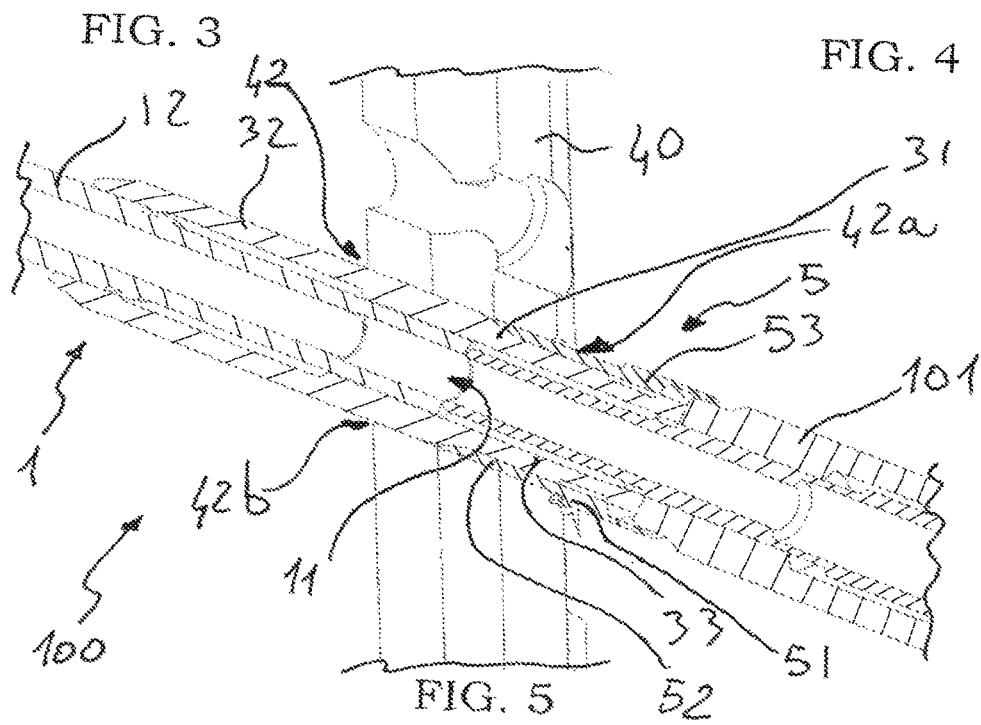

ENDOSSEOUS SCREW ASSEMBLY AND INTERNAL FIXATION SYSTEM COMPRISING SAID ENDOSSEOUS SCREW ASSEMBLY

CROSS-REFERENCE TO RELATED APPLICATION(S)

The present application claims priority under 35 U.S.C. 365 to International Patent Application No. PCT/EP2016/072100 filed Sep. 19, 2016, entitled "Endosseous screw assembly and internal fixation system comprising said endosseous screw assembly", and through International Patent Application No. PCT/EP2016/072100, to European patent Application No. 15425073.2 filed Sep. 29, 2015, each of which are incorporated herein by reference into the present disclosure as if fully set forth herein.

FIELD OF THE DISCLOSURE

The present disclosure is applicable to the field of orthopaedic surgery and relates to an endosseous, or intramedullary, screw assembly, in particular of the type used in internal fixation systems comprising plates or nails.

The disclosure also relates to the internal fixation system comprising said endosseous screw assembly.

BACKGROUND

The internal fixation systems, which are widely used in the orthopaedics sector, embrace different types of bone implants which are generally applied in order to stabilize the fractured bone site of a patient.

The internal fixation systems may comprise a bone plate, which is fixed in contact with an external surface of the fractured bone in order to ensure alignment and fixing of two or more segments thereof. In order to allow fixing of the plate, the system envisages in these cases a plurality of bone screws which pass through a corresponding number of holes formed in the element.

The internal fixation systems may also comprise an endomedullary, or intramedullary, nail which is typically inserted inside the medullary canal of the long bone of a patient. In this case also, generally one or more bone screws are provided, these passing through the bone cortex in the transverse direction and interfacing with the endomedullary nail in order to stabilize the system.

In both types of implant described above, it is required to provide a stable connection between the stem of the screw and the body of the plate or the nail. This connection must be able to transmit onto the plate/nail torsional and flexional stresses which are applied to the screw stem, allowing at the same time controlled axial sliding of said stem so as to allow the screwing and removal operations.

In order to satisfy the aforementioned requirements, connection systems are generally relatively elaborate and complex, so that they constitute a critical phase of the fixation system implant both from the point of view of time and as regards the attention required by the surgeon.

In particular, in the case of a fracture in the tranchanter zone, common practice requires stabilization of the fracture using one or more screws in the neck of the femur and several screws in the middle part of the femur. The screw placed in the neck of the femur usually is large in size and must be able to slide along its axis.

Therefore, the implant of the device requires the surgeon to carry out several consecutive operations aimed at ensuring the correct positioning of the screw inside the femoral neck.

Basically, the devices which are currently widely used require particular attention during insertion of the screw which is performed by means of a special tool, the orientation of which determines the correct insertion thereof into the patient's bone.

For instance, in document US 2014/214098 A1 it is disclosed an elongated modular implant which has a distal part and a proximal part both having a leading end and a trailing end, respectively. The trailing end of the distal part includes a tool engagement portion and the leading end of the proximal part includes a distal part engagement portion for an engagement with the tool engagement portion of the distal part. The implant further includes an assembly element for firmly coupling the distal part and the proximal part.

Consequently, the surgeon is required to carry out different preliminary operations before performing insertion of the screw.

Moreover, the connection of the screw to the plate/nail requires generally, after the aforementioned screw has been implanted, the insertion of a further locking element.

Such a surgical procedure must therefore be carried out with particular attention and unfortunately may not be assigned to surgeons with little experience, despite the fact that such operations are now considered to be routine in the orthopaedics departments of hospitals.

Moreover it is clear how this increases the duration of the operations, with greater risks for the health of patients, in particular if they are elderly.

A technical problem underlying the present disclosure is therefore that of providing an endosseous screw assembly and associated internal fixation system which allow a reduction in the duration of the surgical operations and which may be implanted by means of a limited number of operations carried out by the surgeon; at the same time it is also desirable that the operational methods should be those which are already known to the surgeon so as to be easily applied also by less expert surgeons.

SUMMARY

The aforementioned technical problem is solved by an endosseous screw assembly, or intramedullary screw assembly according to its specific field of application, for an internal fixation system, comprising:
a stem extending longitudinally and having at least one threaded distal portion for allowing anchoring to a bone site of a patient;
a connection sleeve suitable for introduction inside a connection hole of an endomedullary nail;
a ring nut rotatably mounted on one end of the connection sleeve by means of a threaded connection and comprising a rim with teeth designed to cooperate with a step formed on the endomedullary nail in the proximity of the connection hole;
the cooperation between at least one tooth of said rim and said step preventing the rotation of said ring nut with respect to the endomedullary nail when the connection sleeve is introduced into the connection hole of the endomedullary nail;
said ring nut further comprising a plurality of deformable interference means which lie along a conical portion of the connection sleeve hosted inside the connection hole when the connection sleeve is introduced inside the connection hole;

said plurality of deformable interference means being oriented so that relative sliding of the ring nut and the connection sleeve during the screwing action of the ring nut results in deformation of the deformable interference means thus obtaining a contact force between the endomedullary nail and the ring nut inside the connection hole locking the endosseous screw in the connection hole of the endomedullary nail.

Advantageously, the ring nut comprises a distal end, which is internally threaded and seats externally the rim with teeth, and a plurality of flexible fins which form the deformable interference means.

Moreover, the flexible fins project from the distal end and extend longitudinally towards the stem of the endosseous screw assembly, when the ring nut is mounted on the connection sleeve.

It should be noted that the connection sleeve has a first cylinder and a second cylinder with different diameters, which are connected by means of the conical portion; the first cylinder having a greater diameter than the diameter of the second cylinder.

The present disclosure further relates to fixation system comprising at least one endosseous screw assembly according to the previous description and comprising at least one fixation member provided with at least one connection hole designed to receive the connection sleeve of said endosseous screw assembly.

Further characteristic features and advantages will emerge more clearly from the detailed description provided hereinbelow of a preferred, but not exclusive embodiment of the present disclosure, with reference to the attached figures, provided by way of a non-limiting example.

BRIEF DESCRIPTION OF THE DRAWINGS

FIG. 3 shows a perspective view of the internal fixation system according to FIG. 1, in which the fixation member is shown cross-sectioned;

FIG. 4 shows a perspective view of the internal fixation system according to FIG. 1, in which both the fixation member and the endosseous screw assembly are shown cross-sectioned;

FIG. 5 shows a view, on a larger scale, of FIG. 4 with the addition of a screwing tool engaged with the endosseous screw assembly;

DETAILED DESCRIPTION

Figure 1:
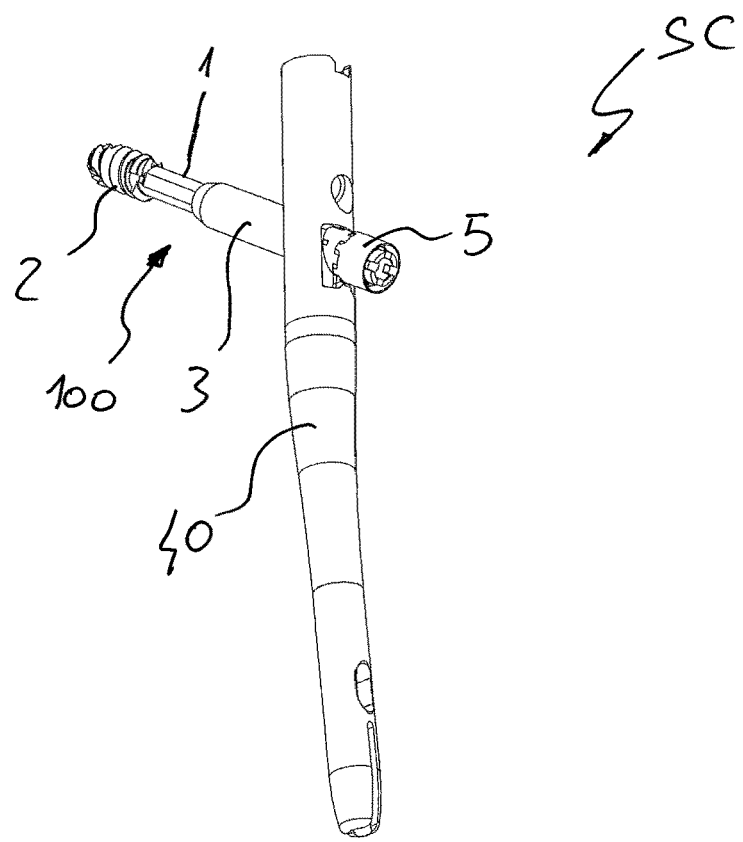
FIG. 1 shows a perspective view of an internal fixation system comprising an endosseous screw assembly according to the present disclosure.
Figure 2:
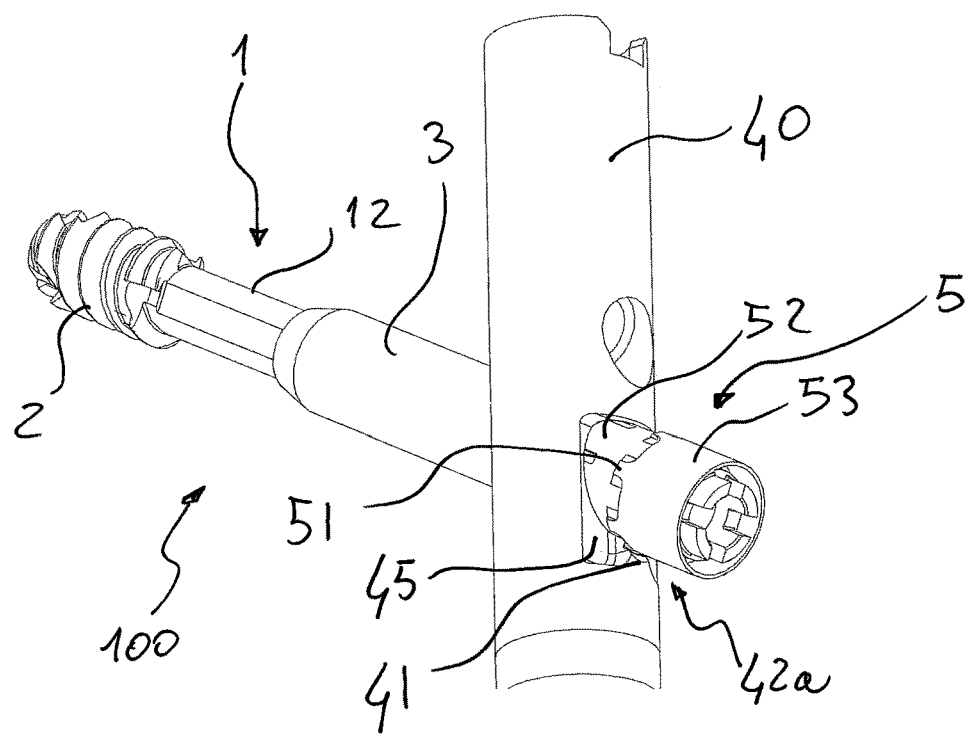
FIG. 2 shows a view, on a larger scale, of FIG. 1.

With reference to the attached figures, and in particular FIGS. 1, 3 and 4, the reference letters SC indicate an internal fixation system in accordance with an embodiment of the present disclosure.

In this embodiment, the internal fixation system SC comprises an endomedullary nail 40, or intramedullary nail 40, in particular a trochanteric nail, and an endosseous screw assembly 100.

The endosseous screw assembly 100 is inserted and locked onto the trochanteric nail 40, inclined with respect to the axis of the nail, in such a way that it is anchored inside the acetabular head of the patient.

In an alternative embodiment, not shown, the fixation system may be a bone plate fixed to the femoral surface of a patient by means of an endosseous screw assembly 100 in accordance with the present disclosure.

Essentially, both the endomedullary nail and the bone plate may be used as internal fixation member, using the same endosseous screw assembly 100.

The internal fixation member 40 has at least one connection hole 42 for locking the endosseous screw assembly 100.

The connection hole 42 for the endomedullary nail 40 will be described in general below.

Figure 9:
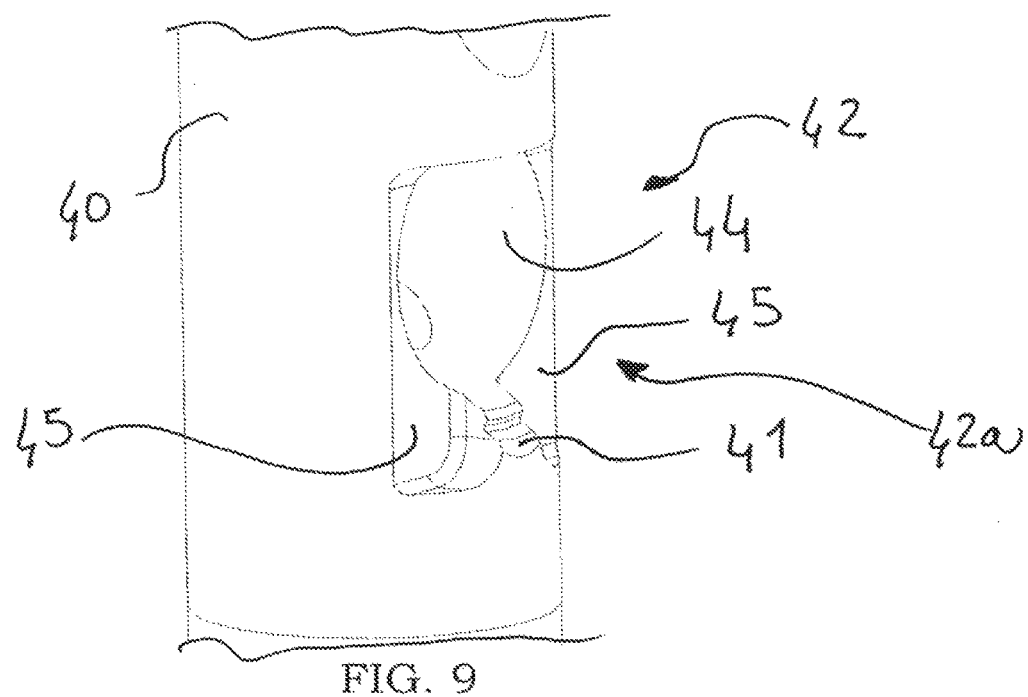
FIG. 9 shows a perspective view of a detail, on a larger scale, of the fixation member according to FIG. 1, in which the endosseous screw assembly according to the present disclosure may be introduced.
Figure 10:
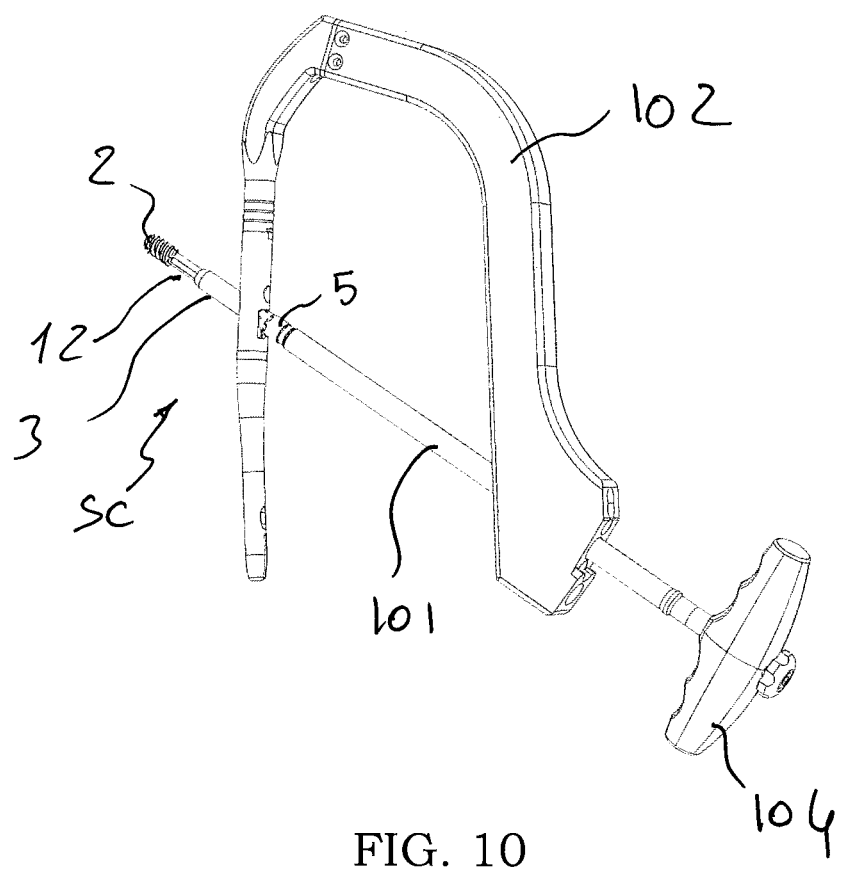
FIG. 10 shows a perspective view of the internal fixation system according to FIG. 1 connected to an associated installation kit.

The connection hole 42, which can be clearly seen in FIG. 9, has an entry side 42a and an exit side 42b for the endosseous screw assembly, or intramedullary screw assembly, which are connected by means of an internal wall 44 and aligned along an axis which defines the inclination of the endosseous screw assembly with respect to the fixation member.

The internal wall 44 of the connection hole, which is substantially circular, defines the internal diameter of the hole.

The entry side 42a has a flattened part which defines a flat surface 45 lying parallel to the longitudinal axis of the fixation system, in the region of the connection hole.

This flat surface 45 is formed in the vicinity of the perimeter of the connection hole, except for a small portion so as to create a step 41 raised with respect to the flat surface. The form and the function of the step 41 will become clear from the following description.

It should be noted that the fixation member 40 may comprise one or more connection holes, so as to allow insertion of a variable number of endosseous screw assemblies, depending on the clinical conditions of the patient, again within the context of the present disclosure.

Figure 6:
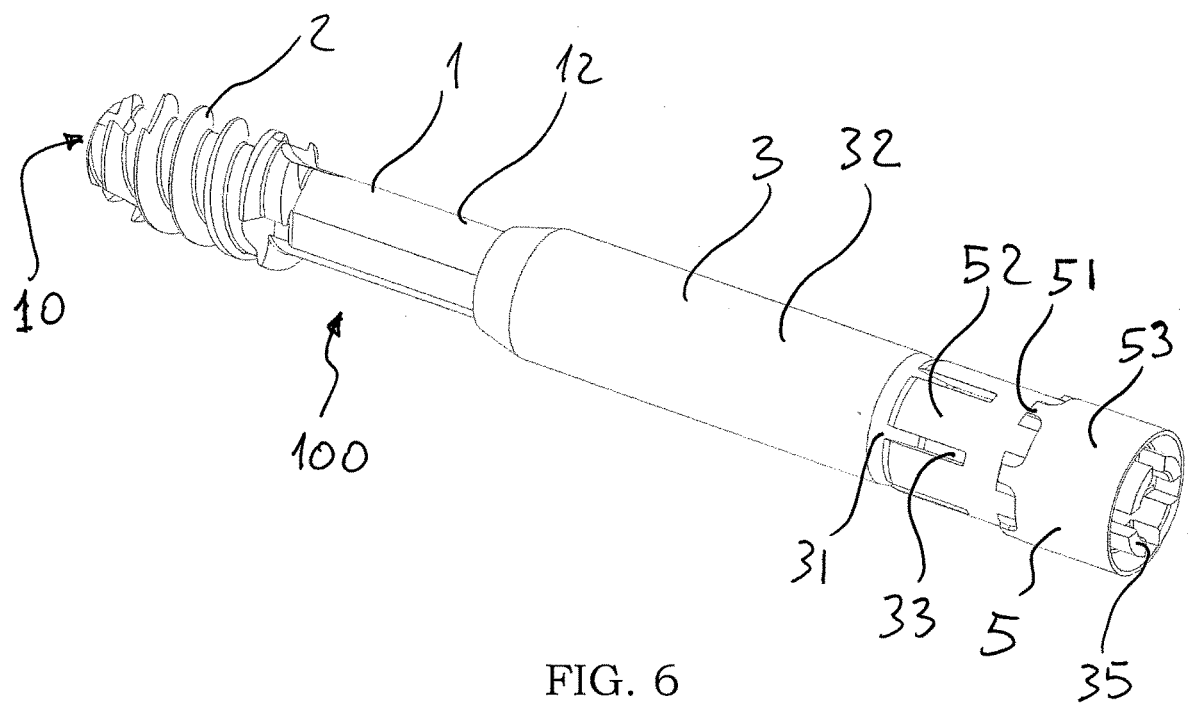
FIG. 6 shows a perspective view of the endosseous screw assembly according to FIG. 1.

The endosseous screw assembly 100, or intramedullary screw assembly 100, which is shown in its entirety in FIG. 6, comprises a longitudinal stem 1 and a connection sleeve 3.

The stem 1 and the connection sleeve 3 may be formed as one piece, so as to be included in a single body forming the endosseous screw assembly. In this case, no relative movement of the stem with respect to the connection sleeve is therefore envisaged.

Alternatively, the stem and the connection sleeve may be formed by two separate bodies with the aforementioned stem partially inserted inside the connection sleeve and movable with respect to the aforementioned connection sleeve.

The stem 1 of the endosseous screw assembly 100 comprises a threaded distal portion 2 and an adjacent cylindrical portion 12.

In the example of embodiment described here, the entire stem 1 is channelled, namely has an axial passage which connects a distal opening 11 to a proximal opening 10. This solution allows the use of a guide wire in order to facilitate insertion of the endosseous screw assembly 100; moreover, the axial passage may advantageously define an access way for injecting in situ a bone substitute or other biological substances.

The threaded distal portion 2 is designed to penetrate into the bone site of the patient and in particular is provided preferably with a self-boring tip which allows the screw to advance in the bone.

The tip has, formed in it, the proximal opening 10 of the aforementioned axial passage, while the distal opening 11 of the axial passage is at the end of the cylindrical portion 12.

The connection sleeve 3 is formed by a hollow body inside which the stem is partly inserted and comprises first and second cylinders 32, 33 with different diameters which are connected by means of a conical portion 31. In particular, the first cylinder 32, in the proximal position, has a diameter greater than that of the second cylinder 33 such that the conicity of the conical portion 31 is directed in the distal direction, substantially away from the stem 1 of the endosseous screw assembly 100.

Preferably, the conical portion 31 of the connection sleeve has a conicity of between 8° and 12°, and preferably equal to 10°.

As already mentioned, if the connection sleeve is formed as a body separate from the stem, the aforementioned stem and connection sleeve are movable relative to each other.

In particular, the connection sleeve 3 is associated in a sliding relationship with the cylindrical portion 12 of the stem 1.

Sliding of the stem 1 is constrained axially in both directions using methods which are known in the sector.

Moreover, the relative rotation of the stem 1 and the connection sleeve 3 is prevented by suitable constraining means which are also known in the sector.

Essentially, the stem 1 may slide within certain limits inside the connection sleeve 3, but is rotationally constrained thereto.

In a preferred embodiment, the connection sleeve has engaging means 35 which are included in the second cylinder 33 and are designed to be joined together with a tool 101 for screwing the threaded distal portion 2 into the bone.

Figure 8:
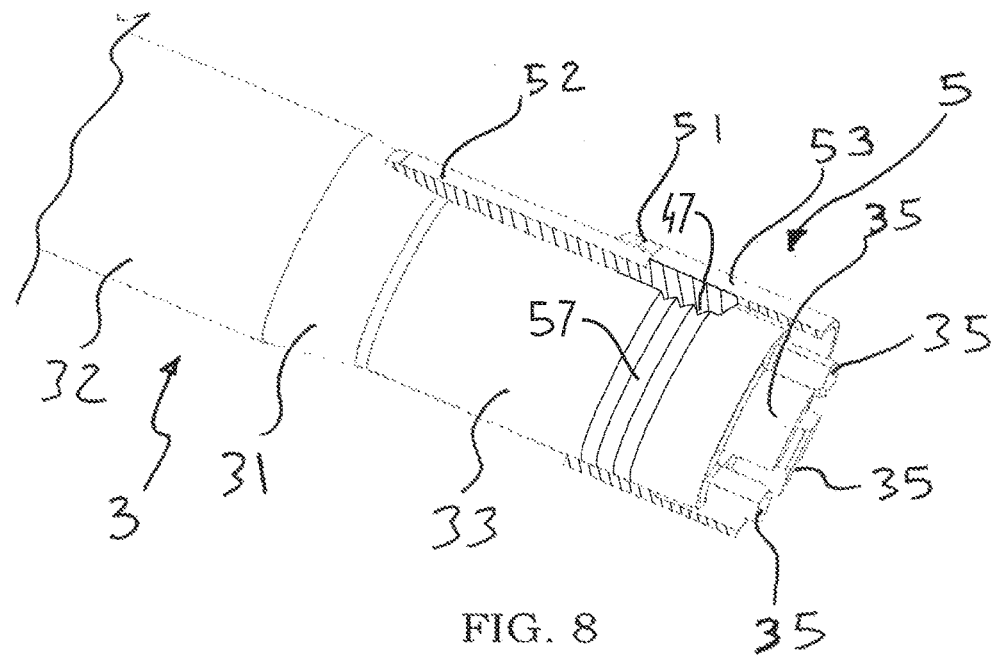
FIG. 8 shows a view, on a larger scale, of FIG. 6 with the ring nut cross-sectioned.

More specifically, as can be seen in FIG. 8, the engaging means 35 take the form of a toothing which projects longitudinally from the distal end of the second cylinder 33 and is shaped so as to reproduce the negative form of the tool for screwing the stem 1.

Figure 11:
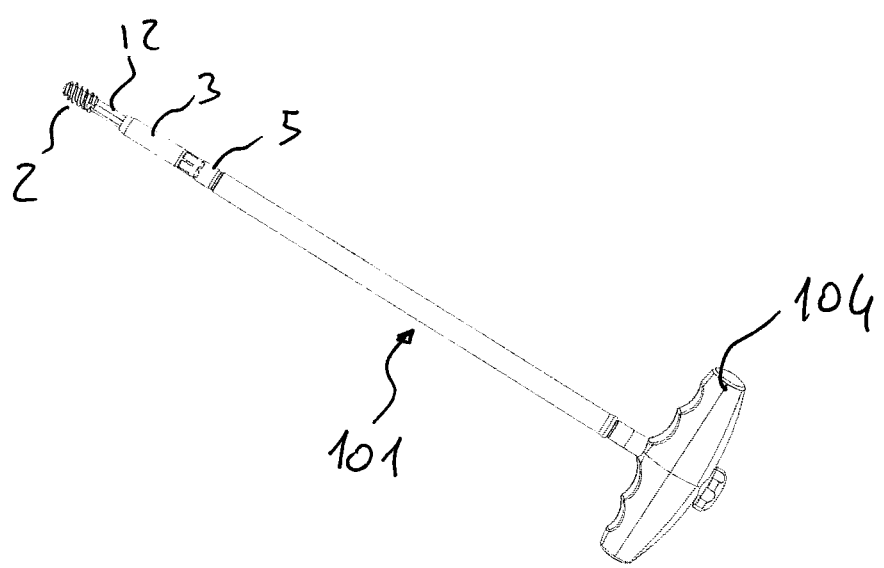
FIG. 11 shows the screwing tool engaged with the endosseous screw assembly.
Figure 12:
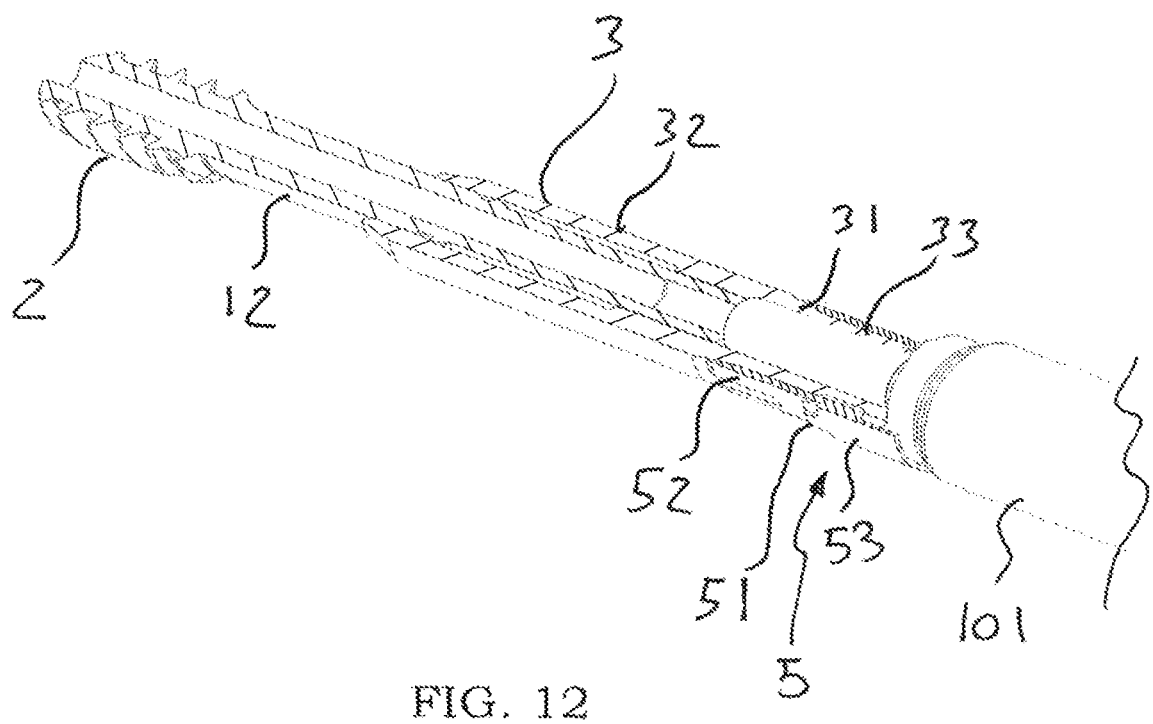
FIG. 12 shows a cross-sectional view of FIG. 11, on a larger scale.

As will be explained more clearly below, the aforementioned tool, which comprises substantially a screwdriver 101 which can be joined together with the engaging means (FIG. 11), also help perform locking of the endosseous screw assembly 42 inside the connection hole 42 of the fixation member 40.

Figure 7:
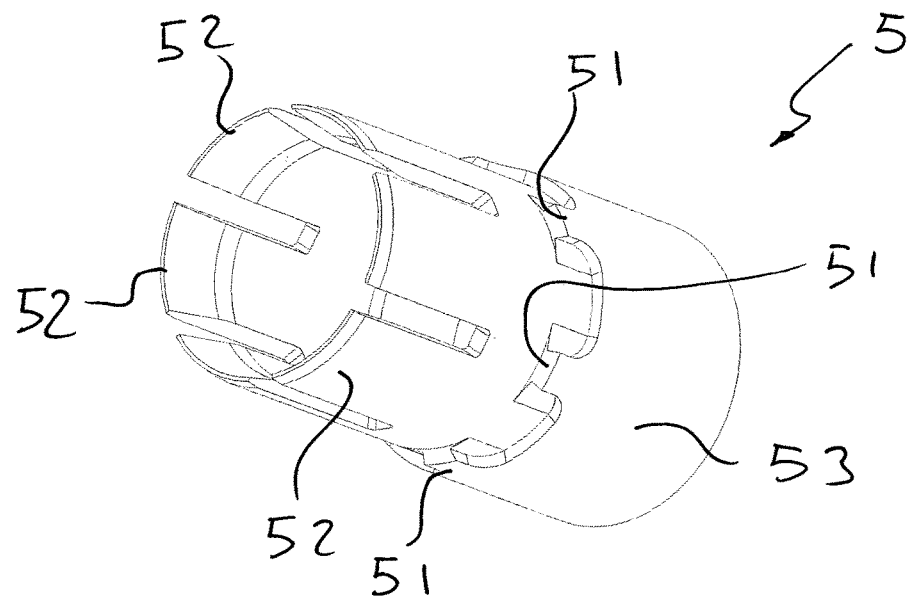
FIG. 7 shows a perspective view of the ring nut of the endosseous screw assembly according to FIG. 1.

The endosseous screw assembly 100, according to the present disclosure, also comprises a ring nut 5 (FIG. 7) which is screwed around the second cylinder 33 of the connection sleeve 3 in the opposite direction to the direction screwing of the threaded distal portion 2 into the bone.

In other words, if the thread of the threaded distal portion 2 is right-handed, the thread 57 of the second cylinder 33 on which the ring nut 5 is screwed is left-handed.

In addition, preferably, the thread of the threaded distal portion 2 is a two-start thread so as to ensure faster insertion into the bone, while the thread 57 of the second cylinder 33 of the connection sleeve 3 is of the single-start type.

The ring nut 5 is formed by an annular body having a distal end 53 with a smooth and continuous outer surface, a proximal end provided with deformable interference means 52, which will be described more clearly below, and a plurality of locking teeth 51 arranged on the outer surface between the proximal end and the distal end of the annular body.

The distal end 53 is internally threaded with threads 47 so as to be able to screwed onto the second cylinder 33 of the connection sleeve 3.

The interference means in the example shown take the form of a plurality of flexible fins 52 which extend longitudinally from the distal end 53 of the annular body 5.

Basically, the proximal end of the annular body has longitudinal cuts which define the fins 52.

These fins 52 are connected to the distal end 53 only at their distal end. Since the ring nut 5 is made of flexible material, the fins 52 are able to flex, such that their free proximal end is able to move elastically in a substantially radial direction.

The fins 52, at their free proximal end, have a tapered internal surface so as to be able to slide along the conical portion 31 of the connection sleeve 3.

Each locking tooth 51 is formed so as to be positioned in contact with the step 41 present on the flat surface of the entry side 42a of the connection hole so as to prevent rotation of the ring nut 5 relative to the fixation member, when the connection sleeve 3 has been fully inserted inside the connection hole.

As can be seen in FIG. 6, the endosseous screw assembly 100, before being inserted into the bone, has the ring nut 5 which is screwed onto the second cylinder 33 with the fins 52 which are positioned along a limited section of the conical portion 31. The larger outer diameter measured on the fins 52 which partially overlap the conical portion 31 does not exceed the outer diameter of the first cylinder 32, as can be seen in FIG. 8.

Operationally speaking, locking of the internal fixation system is performed by inserting the endosseous screw assembly 100 inside the connection hole 42 and rotating the endosseous screw assembly 100 by means of the screwdriver 101 which is engaged with the teeth 55 which project longitudinally from the distal end of the cylinder 33 (FIG. 5).

Basically rotation of the connection sleeve 3 is performed and this transmits the rotation to the threaded distal portion 2 and to the ring nut 5.

When one of the locking teeth 51 of the ring nut 5 comes into contact against the step 41, the ring nut 5 is locked against the fixation member 40.

This locking of the ring nut 5 with respect to the fixation member 40 does not prevent the ring nut 5 from rotating with respect to the connection sleeve 3.

In fact, in this locked position of the ring nut 5 against the flat surface 45 of the fixation member 40, the rotation of the screwdriver 101 in the direction of screwing into the bone of the threaded distal portion 2, causes the relative rotation of the connection sleeve 3 and the ring nut 5, since the latter is locked with respect to the fixation member 40.

Essentially, the connection sleeve 3 rotates with respect to the fixed ring nut 5.

The presence of a left-handed thread in the connection between the connection sleeve 3 and the ring nut 5 causes, while the screwdriver 101 continues to rotate in the clockwise direction, a relative movement of the connection sleeve 3 in the opposite direction to the direction of insertion into the bone, which therefore moves axially in the distal direction, i.e. away from the bone.

The overall movement of the stem 1 with respect to the connection sleeve 3 depends on the length of the bone screw 100 and generally ranges between 5 mm and 25 mm, being preferably 20 mm.

This relative axial movement of the sleeve 3 and the ring nut 5 is instead equal to a few tenths of a millimetre. This latter axial movement, in the distal direction, of the connection sleeve 3, with the ring nut 5 locked on the flat surface 45, causes sliding of the conical position 31 of the connection sleeve 3 underneath the fins 52 of the ring nut 5, with consequent radial displacement of the said fins 52 which, overlapping the conical portion 31, tend to expand externally.

In other words, during the screwing movement of the screw assembly 100, the screw 2 causes the movement also of the connection sleeve 3 and the ring nut 5, and the latter, although being threaded on a left-handed thread, continues to advance (since made to move by the screw 2 as described above) until it is locked on the nail following the conical coupling action or until the surface 45 is reached by the larger diameter of the distal end 53 of the ring nut 5.

Only in this latter case, namely when the advancing movement is prevented by the nail 40, does the left-handed threading between ring nut 5 and connection sleeve 3 produce minimal retraction of the connection sleeve 3 until the ring nut 5 is fully locked on the nail 40.

The amount of the relative movement—albeit equal to tenths of a millimetre—of the ring nut 5 and connection sleeve 3 is due to the number of rotations necessary for locking the ring nut 5 on the connection sleeve 3 following opening of the fins 52 on the conical portion 31.

Since the fins 52 are axially locked inside the connection hole 42, in the locked position of the ring nut 5 on the fixation member 40, the result is that the radial expansion of the fins 52, caused by the retraction of the connection sleeve 3, produces in turn frictional locking between the ring nut 5 and the internal wall 44 of the connection hole 42.

In other words, the conical portion 31 moves underneath the fins 52 which, widening radially with respect to the initial position, push against the internal wall 44 of the connection hole 42, until they block consequently also rotation of the connection sleeve 3.

At this point the screwing operation with the screwdriver 101 is terminated.

Consequently the endosseous screw assembly is locked relative to the fixation member.

It is pointed out that the axial displacement in the distal direction of the connection sleeve may cause a consequent axial displacement in the same distal direction of the threaded distal portion 2 which, as known in the sector, is entirely desirable because it improves the grip on the bone.

Obviously, the internal diameter of the connection hole 42 is chosen so as to allow the fins 52 to be inserted snugly when they rest on the connection sleeve 3, before being splayed.

Preferably, the internal diameter of the connection hole 42 is substantially equivalent to the diameter of the first cylinder 32, with the possibility of the latter sliding freely.

For a person skilled in the art it will be clear how both unscrewing of the ring nut 5 from the connection sleeve 3 and sliding of the ring nut 5 with respect to the internal wall 44 of the connection hole 42 are prevented, when the contact force exceeds a threshold value.

In other words the contact force occurring between the ring nut and the internal wall of the connection hole, not only prevents sliding of the endosseous screw assembly inside the connection hole, but also results in a contact force between the ring nut and the connection sleeve, relative rotation of which is thus prevented.

As mentioned above, the tapered part of the internal surface of the fins 52 forms a receiving surface which facilitates sliding of the aforementioned flexible fins along the conical portion 31 of the connection sleeve 3.

The stem and the connection sleeve are made of biocompatible materials, preferably steel, titanium alloy or titanium. The ring nut, since it must ensure a sufficient elasticity for the deformable interference means, is made preferably of titanium.

In order to provide a complete description of the present disclosure, the method by means of which a surgeon can insert the endosseous screw assembly inside the fractured bone site and lock the endosseous screw assembly on the fixation member is now illustrated.

The implant of the fixation system, as described above, is performed by means of two consecutive steps, during which the surgeon first anchors the fixation member on the fractured bone site and then inserts the endosseous screw assembly through the patient's bone.

During a first anchoring step, therefore, the fixation member, whether it be a trochanteric nail or a plate, is oriented correctly and then fastened to the fractured bone of the patient.

Thereafter, the endosseous screw assembly is inserted inside the connection hole. This operation is performed with the aid of guiding means comprising a handle 102 and a guide tube through which the endosseous screw assembly is slid, being pushed by the abovementioned screwdriver 101.

As can be seen from FIG. 9, the screwdriver 101 is joined to the connection sleeve 3 by means of the engaging means 35, such that the surgeon may perform screwing of the stem inside the bone, when the endosseous screw assembly comes into contact with the bone tissue, exclusively by rotating the aforementioned screwdriver by means of a handle 104.

This operation of screwing the endosseous screw assembly continues until the ring nut 5 comes into contact against the fixation member.

As already mentioned above, in this condition the rotation of the aforementioned ring nut 5 is now prevented by means of the step 41 formed on the entry side of the connection hole and shaped so as to engage a tooth 51 of the ring nut 5.

While rotation of the aforementioned ring nut with respect to the fixation member is locked, the connection sleeve 3 and the stem 1, which are rotationally integral, may however be still rotated by means of the screwdriver 101.

The threaded connection present between the ring nut 5 and the connection sleeve 3 produces, however, relative sliding of the two parts (connection sleeve/ring nut) and in particular retraction of the connection sleeve, since the ring nut 5 is locked in contact therewith and since the thread 57 is formed in the opposite direction.

Therefore, the fins 52 of the ring nut 5 slide along the conical portion 31 of the connection sleeve 3, radially flexing and pushing against the internal wall 44 of the connection hole.

A person skilled in the art will understand how this condition prevents both relative sliding of the ring nut with respect to the internal wall of the connection hole and rotation of the ring nut with respect to the connection sleeve, owing to the contact force present between the endosseous screw assembly and the fixation member inside the connection hole.

A person skilled in the art will understood how the endosseous screw assembly according to the disclosure allows simplification of the procedure for an implant of the corresponding fixation system, reducing both the number of tools and the operations required for the surgical operation.

It can be noted, in fact, how, after introduction of the endosseous screw assembly inside the guide tube, the surgeon may proceed using only the screwdriver.

Similarly, the operation of removal of the endosseous screw assembly is facilitated, requiring again the use of only the screwdriver.

In any case, despite the simplifications introduced, the fixation system will ensure correct supporting on the fracture site.

Advantageously, moreover, the duration of the surgical operations for the implant of these systems will be reduced.

Finally, since the surgeon must carry out a limited number of operations, a non-expert operator will also be able to perform the operation.

Obviously a person skilled in the art, in order to satisfy any specific requirements which might arise, may make numerous modifications and variations to the present disclosure, all of which are contained moreover within the scope of protection of the present disclosure, as defined by the following claims.

What is claimed is:

1. An intramedullary screw assembly for an internal fixation system comprising:
   a stem extending longitudinally and having at least one threaded distal portion for allowing anchoring to a bone site of a patient;
   a connection sleeve suitable for introduction inside a connection hole of a fixation member; and
   a ring nut rotatably mounted on a proximal end of the connection sleeve by means of a threaded connection and comprising a rim portion with teeth cooperating with a step formed on the fixation member in proximity of the connection hole,
   wherein the cooperation between at least one of the teeth of the rim and the step prevents the rotation of the ring nut with respect to the fixation member when the connection sleeve is introduced in the connection hole of the fixation member,
   wherein the ring nut further comprises a plurality of deformable interference means which lie along a conical portion of the connection sleeve seated inside the connection hole when the connection sleeve is introduced inside the connection hole,
   and
   wherein the plurality of deformable interference means is oriented so that relative sliding of the ring nut and the connection sleeve during the screwing action of the ring nut results in deformation of the deformable interference means at an end of the ring nut nearest the threaded distal portion of the stem, thus obtaining a contact force between the fixation member and the ring nut inside the connection hole locking the intramedullary screw assembly inside the connection hole of the fixation member.

2. The intramedullary screw assembly according to claim 1, wherein the ring nut comprises an end portion which is internally threaded and presents externally the rim with teeth, and a further extended portion including a plurality of flexible fins which form the deformable interference means.

3. The intramedullary screw assembly according to claim 2, wherein the flexible fins extend longitudinally towards the threaded distal portion of the stem of the intramedullary screw assembly when the ring nut is mounted on the connection sleeve.

4. The intramedullary screw assembly according to claim 2, wherein the flexible fins are tapered.

5. The intramedullary screw assembly according to claim 2, wherein a circumference defined by the deformable interference means of the ring nut is substantially equivalent to the circumference of the connection hole.

6. The intramedullary screw assembly according to claim 1, wherein the connection sleeve has a first cylinder portion and a second cylinder portion having different diameters and connected by means of the conical portion, and wherein the first cylinder portion has a greater diameter than the second cylinder portion.

7. The intramedullary screw assembly according to claim 1, wherein the conical portion of the connection sleeve has a conicity of between 8° and 12°.

8. The intramedullary screw assembly according to claim 1, wherein the connection sleeve has engaging means suitable for joining together with a screwdriver for performing screwing of the stem.

9. The intramedullary screw assembly according to claim 1, wherein the stem is formed integrally with the connection sleeve.

10. The intramedullary screw assembly according to claim 1, wherein the stem is partially inserted inside the connection sleeve, and wherein the stem is operable to slide but not rotate inside the connection sleeve.

11. The intramedullary screw assembly according to claim 1, wherein the threaded distal portion has a two-start thread, and wherein the threaded connection between the ring nut and the connection sleeve is performed by means of screwing with a single-start thread.

12. A fixation system comprising:
    a first fixation member comprising one or more connection holes, and
    one or more intramedullary screw assemblies, the one or more intramedullary screw assemblies each comprising:
      a stem extending longitudinally and having at least one threaded distal portion for allowing anchoring to a bone site of a patient;
      a connection sleeve suitable for introduction inside one of the one or more connection holes of the fixation member; and
      a ring nut rotatably mounted on a proximal end of the connection sleeve by means of a threaded connection and comprising a rim portion with teeth cooperating with a step formed on the fixation member in proximity of one of the one or more connection holes,
    wherein the cooperation between at least one of the teeth of the rim and the step prevents the rotation of the ring nut with respect to the fixation member when the connection sleeve is introduced in one of the one or more connection holes of the fixation member,
    wherein the ring nut further comprises a plurality of deformable interference means which lie along a conical portion of the connection sleeve seated inside one of the one or more connection holes when the connection sleeve is introduced inside one of the one or more connection holes,
    and
    wherein the plurality of deformable interference means is oriented so that relative sliding of the ring nut and the connection sleeve during the screwing action of the ring nut results in deformation of the deformable interference means at an end of the ring nut nearest the threaded distal portion of the stem, thus obtaining a contact force between the fixation member and the ring nut inside one of the one or more connection holes, thereby locking the intramedullary screw assembly inside one of the one or more connection holes of the fixation member.

13. The fixation system according to claim 12, wherein one or more connection holes have a flattened part including the step extending in a raised position with respect to the flattened part.

14. The fixation system according to claim 12, wherein the first fixation member is a trochanteric nail or a plate.

15. The fixation system according to claim 12, further comprising a handle and a screwdriver for screwing the stem of one of the one or more intramedullary screw assemblies into one of the one or more connection holes.

16. An intramedullary screw assembly for an internal fixation system, comprising:
a stem extending longitudinally and having at least one threaded distal portion for allowing anchoring to a bone site of a patient;
a connection sleeve suitable for introduction inside a connection hole of an intramedullary nail; and
a ring nut rotatably mounted on one end of the connection sleeve by means of a threaded connection and comprising a rim with teeth designed to cooperate with a step formed on the intramedullary nail in proximity of the connection hole,
wherein the cooperation between at least one of the teeth of the rim and the step prevents the rotation of the ring nut with respect to the intramedullary nail when the connection sleeve is introduced into the connection hole of the intramedullary nail,
wherein the ring nut further comprises a plurality of deformable interference means which lie along a conical portion of the connection sleeve hosted inside the connection hole when the connection sleeve is introduced inside the connection hole,
and
wherein the plurality of deformable interference means are oriented so that relative sliding of the ring nut and the connection sleeve during the screwing action of the ring nut results in deformation of the deformable interference means at an end of the ring nut nearest the threaded distal portion of the stem thus obtaining a contact force between the intramedullary nail and the ring nut inside the connection hole locking the intramedullary screw in the connection hole of the intramedullary nail.

17. The intramedullary screw assembly according to claim 16, wherein the ring nut comprises a distal end portion which is internally threaded and has a plurality of flexible fins which form the deformable interference means.

18. The intramedullary screw assembly according to claim 17, wherein the flexible fins form the distal end portion of the ring nut and extend longitudinally towards the threaded distal portion of the stem of the intramedullary screw assembly when the ring nut is mounted on the connection sleeve.

19. The intramedullary screw assembly according to claim 17, wherein the flexible fins are tapered.

20. The intramedullary screw assembly according to claim 17, wherein the stem is partially inserted inside the connection sleeve such that the stem is able to slide, but not rotate inside the connection sleeve.

21. The intramedullary screw assembly according to claim 16, wherein the connection sleeve has a first cylinder portion and a second cylinder portion with different diameters which are connected by means of a conical portion, and wherein the first cylinder portion has a greater diameter than the second cylinder portion.

22. The intramedullary screw assembly according to claim 21, wherein the conical portion of the connection sleeve has a conicity of between 8° and 12°.

23. The intramedullary screw assembly according to claim 16, wherein the connection sleeve has engaging means suitable for joining together with a screwdriver for performing screwing of the stem.

24. The intramedullary screw assembly according to claim 16, wherein the stem is formed integrally with the connection sleeve.

25. The intramedullary screw assembly according to claim 16, wherein an external circumference defined by the deformable interference means of the ring nut is equivalent to the circumference of the connection hole.

26. The intramedullary screw assembly according to claim 16, wherein the distal portion of the stem has a two-start thread, while the threaded connection between the ring nut and the connection sleeve is performed by means of screwing with a single-start thread.

27. A fixation system comprising:
an intramedullary nail comprising one or more connection holes, and
one or more intramedullary screw assemblies for the fixation system, the one or more intramedullary screw assemblies each comprising:
a stem extending longitudinally and having at least one threaded distal portion for allowing anchoring to a bone site of a patient;
a connection sleeve suitable for introduction inside one of the one or more connection holes of the intramedullary nail; and
a ring nut rotatably mounted on one end of the connection sleeve by means of a threaded connection and comprising a rim with teeth designed to cooperate with a step formed on the intramedullary nail in proximity of one of the one or more connection holes,
wherein the cooperation between at least one of the teeth of the rim and the step prevents the rotation of the ring nut with respect to the intramedullary nail when the connection sleeve is introduced into one of the one or more connection holes of the intramedullary nail,
wherein the ring nut further comprises a plurality of deformable interference means which lie along a conical portion of the connection sleeve hosted inside one of the one or more connection holes when the connection sleeve is introduced inside one of the one or more connection holes,
and
wherein the plurality of deformable interference means are oriented so that relative sliding of the ring nut and the connection sleeve during the screwing action of the ring nut results in deformation of the deformable interference means at an end of the ring nut nearest the threaded distal portion of the stem thus obtaining a contact force between the intramedullary nail and the ring nut inside one of the one or more connection holes locking the intramedullary screw in one of the one or more connection holes of the intramedullary nail.

28. The fixation system according to claim 27, wherein the one or more connection holes has a flattened part including a step extending in a raised position with respect to the flattened part.

29. The fixation system according to claim 27, further comprising a handle and a screwdriver for screwing the stem of one of the one or more intramedullary screw assemblies into one of the one or more connection holes.

* * * * *